United States Patent [19]

Verani

[11] Patent Number: 6,026,317
[45] Date of Patent: Feb. 15, 2000

[54] MYOCARDIAL PERFUSION IMAGING DURING CORONARY VASODILATION WITH SELECTIVE ADENOSINE $A_2$ RECEPTOR AGONISTS

[75] Inventor: Mario S. Verani, Houston, Tex.

[73] Assignee: Baylor College of Medicine, Houston, Tex.

[21] Appl. No.: 09/020,121

[22] Filed: Feb. 6, 1998

[51] Int. Cl.[7] ..................................................... A61B 6/00
[52] U.S. Cl. ............................. 600/420; 600/431; 514/46
[58] Field of Search .................................... 600/431, 436, 600/437, 420, 425, 407; 424/9.1–9.8; 250/363.02; 514/45, 46

[56] References Cited

U.S. PATENT DOCUMENTS

| | | | |
|---|---|---|---|
| 4,968,697 | 11/1990 | Hutchison | 514/46 |
| 5,070,877 | 12/1991 | Mohiuddin et al. | 600/420 |
| 5,251,621 | 10/1993 | Collins | 607/4 |
| 5,424,297 | 6/1995 | Rubio et al. | 514/46 |
| 5,477,857 | 12/1995 | McAfee et al. | 600/431 |
| 5,629,298 | 5/1997 | Dobson, Jr. | 514/45 |

*Primary Examiner*—William E. Kamm
*Assistant Examiner*—Ali M. Imam
*Attorney, Agent, or Firm*—Fulbright & Jaworski L.L.P.

[57] ABSTRACT

Potent pharmacological coronary vasodilators, of the family of compounds represented by the known compound CGS-21680, as an adjunct in the detection of coronary artery disease form the basis of this application.

23 Claims, No Drawings

MYOCARDIAL PERFUSION IMAGING DURING CORONARY VASODILATION WITH SELECTIVE ADENOSINE A₂ RECEPTOR AGONISTS

BACKGROUND OF THE INVENTION

1. Technical Field of the Invention

The subject matter of this patent is the diagnostic use of selective adenosine receptor agonists as artificial or pharmacologic stressors to assess myocardial perfusion and function.

2. Prior Art

Persons having or whom are suspected of having coronary artery disease are often referred for diagnostic tests known as myocardial perfusion imaging procedures. This family of procedures comprises powerful diagnostic tools for determining both the presence and extent of coronary artery disease. The rationale behind these procedures is that certain cardiac abnormalities may not manifest themselves at rest (i.e., the patient is in the normal or unexerted state), though their presence will become apparent if oxygen demand is increased so that the blood flow through the heart increases (for instance, during vigorous exercise). Thus, though an arterial occlusion may be too small to affect blood flow through the heart at rest-when flow rate is low-the presence of the occlusion is much more likely to become apparent if blood flow is increased. Therefore, myocardial function is often assessed while the patient is under stress, or conditions of increased blood flow through the major vessels.

One very common means of inducing stress is to have the patient walk on a treadmill. Once the desired blood flow levels are achieved through the suspected occluded regions, blood flow through this region(s) is monitored. One means by which this monitoring can occur is by injecting the patient with a compound known as a tracer, such as thallium-201. This is a radioactive compound, thus, its presence is observable by typical radiation-detection devices positioned near the patient. Since the tracer is quickly removed from the bloodstream, and absorbed by the heart muscle cells, and since the concentration of the tracer at a given location in the heart muscle is proportional to the amount of blood flowing through the vessel, it is, therefore possible—by observing the amount of tracer into the heart muscle—to indirectly monitor the blood through the vessel of interest. Low levels of blood flow—as evidenced by low tracer levels—at a certain point in the vessel may indicate an occlusion.

Yet many patients with suspected or documented coronary artery disease are unable to exercise, thus it is desirable to induce myocardial stress (to increase blood flow through the heart) by an "artificial" means. This is the function of pharmacological stressors, such as those disclosed in the method of the present Invention. These chemical compounds, upon administration to a patient, mimic the effects of exercise, thus they allow the physician to detect the presence of myocardial occlusions, as blood flow through the suspected occluded region is transferred.

At the present time, two pharmacological stress agents are approved by the FDA, for use as adjuncts to myocardial perfusion imaging. These are adenosine and dipyridamole. Additionally, in a 1993 review article, one investigator listed several viable candidates: adenosine, dipyridamole, and dobutamine. Verani, M. S., *Pharmacologic Stress Myocardial Perfusion Imaging*, 28 Cur. Probs. in Cardiol. 481 (1993). Additional perfusion imaging agents have also been the subject of patent applications. U.S. Pat. No. 5,477,857, by McAfee et al. and assigned to Discovery Therapeutics, Inc., discloses methods for diagnosing myocardial dysfunction based on hydrazinoadenosine-based compounds. Similarly, U.S. Pat. No. 5,070,877, by Mohiuddin and Hillerman, and assigned to MeDco Research, Inc. discloses the use of adenosine as a myocardial perfusion agent to detect coronary disease.

Adenosine is the current state-of-the-art pharmacological stressor for use in myocardial imaging. The efficacy of adenosine in diagnosing coronary artery disease has been well-studied. Verani, M. S., Mahmarian, J. J., Hixson, J. B., Boyce, T. M., Staudacher, R. A., *Diagnosis of Coronary Artery Disease by Controlled Coronary Vasodilation With Adenosine and Thallium-201 Scintigraphy in Patients Unable to Exercise*, 82 Circulation 80 (1990); Mahmarian, J. J., Mahmarian, A. C., Marks, G. F., Pratt, C. M., Verani, M. S., *Role of Adenosine Thallium-201 Tomography for Defining Long-Term Risk in Patients After Acute Myocardial Infarction*, 25 JACC 1333 (1995). In addition, its safety, quite naturally, has been the subject of intensive study. Korkmaz, M. E., Mahmarian, J. J., Guidry, G. W., Verani, M. S., *Safety of Single-Site Adenosine Thallium-201 Scintigraphy*, 73 Amer. J. of Cardiol. 200 (1994). Finally, although other candidates, such as those disclosed above, have been suggested as possible replacements for adenosine, no successful replacement has yet been found, despite the promising experimental data based on these compounds. This fact illustrates the highly unpredictable nature of compounds of this type when used for this particular purpose. Indeed, while efficacy may, in certain instances, be easier to predict, the broad spectrum of potential (and potentially life-threatening) side effects is far, far more difficult to predict.

The pharmacological activity of both adenosine and dipyridamole, as it relates to myocardial perfusion imaging, results from stimulation of the adenosine $A_{2A}$ receptors. Yet these two compounds are nonselective for this receptor, and also bind to the $A_1$ and $A_3$ adenosine receptors. According to the current orthodoxy, this nonselective binding—or binding to receptors other than the target receptor—is largely responsible for the numerous side effects that these two compounds exhibit. The uncertainty of this statement should not be dismissed; in other words, a compound that binds more selectively to the $A_{2A}$ receptor is not necessarily a superior candidate for a pharmacological. Indeed, as in nearly all facets of biomedical research, the actual results are quite unpredictable.

Again, nonspecific binding, or binding to other than the $A_{2A}$ receptor is thought to be responsible for many of the undesirable side effects of pharmacological stressors, most notably adenosine. Some of these side effects are potentially serious, including advanced-degree atrioventricular block. Verani, M. *Adenosine Stress Imaging*, 3 Coronary Artery Disease 1145, 1147 (1992).

Therefore, a compound that exhibits, among other things, high selectivity towards the $A_{2A}$ receptor is highly desirable for further investigation as a possible candidate for an improved pharmacological stressor. The family of compounds disclosed in this Application are based on 2-p-(2-Carboxymethyl)phenethylamino-5'-N-ethylcarboxamidoadenosine hydrochloride, known commercially as CGS-21680. The compounds known as CGS-21680 has been previously disclosed. In addition, the greater selectivity of CGS-21680 over adenosine for the $A_{2A}$ receptor (i.e., greater binding to the $A_{2A}$ receptor and less to the $A_1$ receptor). According to one study from the prior art, CGS-21680 exhibits a 170-fold selectivity for $A_{2A}$ over the $A_1$ receptor. Jarvis, M. F., Schulz, R. Hutchinson, A. J., Do, U. H., Sills, M. A., Williams, H. [$^3$H]CGS 21680, a selective $A_2$ receptor agonist directly labels $A_2$ receptors in rat brain. 251 J. Pharmacol. Exp. Ther. 888 (1989). In addition, the potent vasodilator effect of CGS-21680 has likewise been previously disclosed. Yet its use as a pharmacologic stressor has not previously been disclosed nor suggested. Though the link between a compound's vasodilatory activity and its efficacy as a pharmacologic stressor is highly unpredictable, the present Invention discloses the use of CGS-21680 and related compounds for use as pharmacologic stressors.

SUMMARY OF THE INVENTION

The primary object of the present Invention is to provide a method for determining myocardial perfusion and dysfunction comprising administering to a patient suspected of having coronary artery disease, the compound CGS-21680, in an amount appropriate to achieve near maximum coronary vasodilation.

The compounds comprising the CGS-21680 family possess a number of advantages over the prior art. These advantages have been uncovered by the inventors of the present Invention; the supporting data are recited later.

Several studies reported in the scholarly literature demonstrate that CGS-21680 is not only a more potent vasodilator than adenosine, but that it is also a more selective $A_{2A}$ receptor agonist. Thus CGS-21680 is, simultaneously both a more potent compound, thus displaying superior diagnostic efficacy, yet exhibit less adverse side effects.

One significant advantage of the family of compounds represented by CGS-21680 over adenosine, the current benchmark for pharmacologic coronary vasodilators, is that the former causes less change in the patients hemodynamic parameters (heart rate and blood pressure). In addition numerous side effects from adenosine administration have been reported, including facial flushing, chest pain, nausea, neck pain, epigastric pain, and so forth. Most likely, these complaints result generally from adenosine's lack of complete selectivity for the $A_{2A}$ receptor. Again, due to the greater selectivity of CGS-21680 towards this receptor, less side effects of this type are anticipated in humans upon CGS-21680 administration.

An additional significant advantage of CGS-21680 and related compounds is that due to its longer half-life compared with adenosine, it can be administered as a bolus injection, in addition to continuous infusion. By contrast, adenosine, which has an ultra-short half-life (<2 seconds) must be administered as a continuous infusion when used as an adjunct to myocardial perfusion scintigraphy.

DETAILED DESCRIPTION OF THE PREFERRED EMBODIMENTS

CGS-21680 is manufactured and sold by Research Biochemicals International ("RBI"), Catalog No. C-141, located in Natick, Mass. 01760-2447, U.S.A., with permission from Ciga-Geigy, the assignee of the patent covering the CGS-21680 structure, U.S. Pat. No. 4,968,697, herein incorporated into the present Application by reference.

The family of compounds utilized in the method of the present Invention are disclosed in the '697 patent. This patent discloses those compounds for use as antihypertensives, based on their selective binding to the $A_{2A}$ receptor. The present Invention is premised on the insight that those compounds can be used in an unrelated context, diagnosis of coronary disease, and more specifically, for instance, as an adjunct to perfusion scintigraphy. The use disclosed in the '697 patent and the use to which the present Invention is directed, is based the vasodilatory effect of the compounds, particularly CGS-21680. Yet the use of CGS-21680 as a vasodilator in conjunction with myocardial perfusion scintigraphy is completely unrelated and not suggested by the compound's efficacy in treating high blood pressure. A suitable candidate for perfusion scintigraphy must not only vasodilate, but must also do so to an extent that coronary flow is dramatically increased so that observable myocardial perfusion heterogeneities occur, which indicate narrowing of the coronary vessel, and hence the presence of coronary disease. So for instance, a compound may cause mild vasodilation and therefore decrease blood pressure thus making it a suitable candidate for an antihypertensive agent (high blood-pressure medicine); however, the degree of vasodilation caused may be insufficient permit the compound's use in perfusion scintigraphy.

One typical clinical application of the method of the present Invention will now be illustrated and explained. In summary, the method consists of the following steps: measuring blood pressure and heart rate at rest, administering the vasodilator, injecting a tracer, then imaging the heart to locate perfusion heterogeneities. Wherever possible, the method of the present Invention will be compared against the adenosine protocol. Again, adenosine is the gold standard for pharmacological coronary vasodilators.

The most essential step involves administering the coronary vasodilator, which in the present Invention, is CGS-21680 and structurally related compounds.

Prior to administration of the vasodilator, flow rate through a given vessel is estimated based on the tracer distribution in the heart muscle while the heart is at rest, that is, without the administration of a vasodilator. The flow rate is then estimated again after administration of a vasodilator (e.g., either adenosine or CGS-21680). In a normal vessel— i.e., one with little or negligible narrowing-the observed increase will be on the order of three to five times resting flow rate. Indeed, this is evidenced, by comparing of the data in column 2 with the data in column 3. For instance, for the average flow in the circumflex coronary artery, adenosine increased the flow over the average of all regions of the heart vessel (trans) by over 3 times (1.81/0.56). This ratio is reported in the adjacent column as the flow reserve. For the same vessel, the flow rate increased over 5 times after CGS-21680 administration. The reason that flow reserve is an important parameter for determining coronary disease is that, for a vessel with narrowing, the flow reserve (ratio of the resting flow over the enhanced flow due to administration of a vasodilator) is less than for a normal vessel. Moreover, measuring flow at different regions of the heart, which receive their blood supply from different vessels (Cx and LAD) enables the clinician to determine the extent and location of the narrowing.

Again, the essence of present Invention is the use of CGS-21860 as potent vasodilator for use in detecting coronary artery disease. Once the agent is administered, vasodilation occurs, then a method for detecting the abnormalities is needed. Thus, the method of the present Invention can be coupled with numerous such techniques, well known to the skilled cardiologist. The preferred method is myocardial perfusion scintigraphy. This method involves injecting the patient with a mildly radioactive tracer, sometime after (or during) injection of the vasodilator. Other methods are contrast echocardiography, magnetic resources imaging or ultrafast computed tomography.

Several types of tracers can be used in the method of the present Invention. One preferred tracer is Tl-201, primarily because it exhibits the highest extraction rate (the amount taken up by the myocardium) compared with the other tracer candidates. Thallium-201 exhibits extraction rates of about 85% on the first pass, compared with about 60% for sestamibi. On the other hand, thallium-201 has a relatively long half-life ($t_{1/2}$) meaning that it must be given in small doses. By contrast, the technetium-99m tracers have a much shorter $t_{1/2}$, though a lower extraction rate. Thus, in the case of the adenosine protocol, clinicians often select Tc-based tracers for heavier patients, for whom more tracer is required, and Tl for lighter patients. The tracer is injected at about three minutes after completing the injection of CGS-21680, followed by imaging by standard methods known to the skilled clinician. The imaging is typically performed in two distinct steps: early imaging, performed immediately after injection of the tracer; and later, redistribution imaging, typically performed about 4 hours later.

A comparison of prior studies with adenosine (another myocardial perfusion agent, and currently the premiere such agent) using dogs, with later clinical results using adenosine protocols in humans, allows the skilled clinical to determine with confidence, safe ranges of the crucial parameters, within reasonable clinical tolerances, for the method of the present Invention, when applied to human subjects. In other words, the extrapolation from dogs to humans is facilitated for the method of the present Invention, because such an extrapolation has previously been performed the essentially the same general method though using adenosine rather than CGS-21680, the compound of the present Invention.

The following two working examples describe the results of experiments performed using open-chest dogs, designed to test the efficacy of CGS-21680 in detecting the presence of coronary narrowings. In each study, an artificial narrowing was produced in each dog to mimic a natural narrowing in humans. Thus, a coronary stenosis was produced in the left anterior descending artery (LAD) to abolish reactive hyperemia though without changing the baseline flow.

EXAMPLE 1

This example presents results from a myocardial scintigraphy study using nine adult mongrel dogs, conducted for the purpose of demonstrating the efficacy of a method of myocardial perfusion imaging utilizing CGS-21680. Briefly, this study involved creating a partial artificial blockage in one coronary artery of a dog, measuring resting flow rates to establish a reliable baseline, injecting the vasodilator agent (either adenosine or CGS-21680) followed by the tracer, then taking images to assess, among other parameters, the enhanced flow rate due to the vasodilator agent.

First, each dog was secured then anesthetized with sodium pentobarbital (30 mg/kg), intubated, and ventilated on a respirator with positive end-expiratory pressure of 4 cm $H_2O$. Arterial blood gases were monitored and pH, $pO_2$, $pCO_2$, and $HCO_3$ levels were maintained at physiological levels. Lead II of the electrocardiogram was monitored continuously. The right femoral vein was cannulated with an 8F polyethylene catheter for the administration of fluids, medications, and the tracers: sestamibi and thallium-201. Both femoral arteries were also be isolated and cannulated with an 8F polyethylene catheter to serve as site for the collection of arterial blood samples for microsphere reference blood withdrawal and for continuous monitoring of systemic arterial pressure.

A thoracotomy was then performed at the level of the fifth intercostal space, and the heart suspended in a pericardial cradle. A flare-tipped polyethylene catheter was then inserted into the left atrial appendage for continuous left atrial pressure measurements and as a site for the injection of radio-labeled microspheres. The left anterior descending coronary artery (LAD) was dissected free of the epicardium, and an ultrasonic flow probe and snare ligature placed around the vessel. A similar flow probe was placed around the left circumflex artery (LCx).

Next, a stenosis (artificial blockage to create narrowing of the vessel) was produced in the left anterior descending artery (LAD) to abolish reactive hyperemia without changing the baseline blood flow.

At this point, baseline measurements can be obtained. During the baseline period, a first set of microspheres (50 mCi) was administered to measure baseline blood flow. The microspheres were labeled with either Sr-85, Nb-95, Cr-51 or Sc-46. The selection order of microspheres was randomized to minimize bias. Contemporaneous with the microsphere administration, a two-minute reference blood sample was drawn from a femoral arterial catheter. To measure the normal reactive hyperemic response, the LAD was briefly occluded by tightening the snare occluder for 10 seconds and releasing it for a reactive hyperemia flow tracing on the strip-chart recorder.

An intravenous infusion of adenosine was begun at a rate of 300 µg/kg/min and continued until LCx flow was maximal. This dose of adenosine was chose to produce high coronary flows without decreasing systolic arterial pressure below 85 mm Hg. When maximal LCx flow was achieved, a second set of microspheres was injected and a reference blood sample was withdrawn for two minutes from the femoral arterial catheter. The intravenous infusion of adenosine was then stopped two minutes after the injection of microspheres.

So that the same dog could be used to study both adenosine and CGS-21680, the adenosine was allowed to clear, thus a second baseline period was established. In every instance, the flow parameters were within error limits of the first baseline. When the LCx and distal LAD flows return to the baseline level, a third set of microspheres was injected, and the reference blood sample was withdrawn for two minutes from the femoral arterial catheter. Then, CGS-21680 infusion was begun at a dose of 0.25 µg/kg per minute and increased until maximal LCx flow is achieved without decreasing systemic arterial pressure below 85 mm Hg (the maximal dose in humans is expected to be between 0.25 and 2.5 µg/kg/min). At the maximal dose of CGS-21680, the LCx and distal LAD flow were recorded, then 0.5 mCi of thallium-201, 5 mCi of sestamibi and microspheres were simultaneously injected, and the reference blood sample withdrawn for two minutes from the femoral arterial catheter again. Two minutes later, planar scintigraphic imaging was performed using the peak photon energy for technetium-99m (140 keV) in the anterior and 45° left anterior oblique views with five minute acquisition for each view. The dogs were then killed.

The heart from each dog was removed and sliced into four rings of approximately one cm thickness from the apex to the base. The slices were trimmed of excess fat and adventitia and placed on a thin piece of cardboard covered with cellophane wrap. The slices were imaged directly on the collimator of a conventional planar gamma camera with the peak photon energy of 140 keV with 20% window for technetium-99m. The defect magnitude may be calculated as a ratio of the average counts in the LAD region over the average counts in the normal LCx region.

To measure thallium-201 and sestamibi activities and microsphere-determined flow in the myocardial tissue samples, each of the four myocardial slices was divided into eight transmural sections, which will were then further subdivided into epicardial, midwall, and endocardial segments, resulting in a total 96 myocardial segments for each dog. The myocardial tissue samples were counted in a gamma-well scintillation counter for technetium-99m within 24 hours and for thallium-201 between 48 to 72 hours of sample collection. The samples were recounted for microsphere flows 2 weeks later upon decay of the thallium-201 and technetium-99m. The tissue counts (dpm/g) were corrected for background, decay, and isotope spillover. The microsphere content in the two-minute reference blood collection (dpm/mL/min) was used to calculate absolute flow (mL/kg/min). Regional myocardial blood flow was then calculated.

The regional flows within the normal LCx and distal LAD beds were determined with microspheres during maximal coronary vasodilation with CGS-21680 and compared to those with adenosine. The myocardial thallium-201 and sestamibi uptake (represented as the percentage of the maximal myocardial counts) within the distal LAD beds during coronary vasodilation with CGS-21680 were compared. Correlations between the microspheres-determined flow and thallium-201 or sestamibi counts were then analyzed.

All data are presented as the mean and standard deviation. Difference between the means of two groups were tested using paired t-test, or Wilcoxon signed rank test. Correlations between the microsphere flows and sestamibi or thallium counts were computed using regression analysis.

The results are immediately below in Table 1:

TABLE 1

|  | Baseline 1 | adenosine | Baseline 2 | CGS |
|---|---|---|---|---|
| Heart Rate (bpm) | 119 ± 24 | 108 ± 14 | 109 ± 20 | 127 ± 22 |
| Systolic Bp (mmHg) | 123 ± 23 | 90 ± 26 | 119 ± 19 | 106 ± 24 |
| Diastolic BP (mmHg) | 99 ± 20 | 65 ± 19 | 96 ± 17 | 71 ± 12 |
| LAD/Cx flow ratio | .84 ± .11 | .36 ± .12 | .99 ± .41 | .32 ± 10 |

Table 1 illustrates the efficacy of GS-21680 compared with adenosine, when utilized in the method of the present Invention. This efficacy is evidenced by the LAD/Cx flow ratio, which is slightly lower for CGS than for adenosine. What this parameter measures is the flow rate through the artificially occluded vessel divided by the flow rate over the normal vessel. Ultimately the desired endpoint of any vasodilator is to achieve maximum flow with the least side effects. The higher the flow rates, then the greater is the difference between LAD flow and Cx flow, since the former is artificially occluded. Therefore, a pharmacologic agent having a superior efficacy will have a lower LAD/Cx ratio, compared with some baseline standard. In other words, the LAD/Cs ratio expresses a particular perfusion's agent ability to reveal a coronary obstruction, whether in dogs or in humans. Indeed, this is observed with CGS compared with adenosine, though the difference is only slight: 0.32 compared with 0.36.

Second, this Table also displays relevant hemodynamic data-heart rate systolic blood pressure, and diastolic blood pressure-for the two vasodilators, compared with the resting baseline. As evidenced by this data, CGS exerts its effect with less decrease in systolic blood pressure (BP) compared with adenosine (13 versus 33 mm decrease). Therefore, in the presence of a significant coronary stenosis, the potent, selective coronary vasodilator effect of CGS-21680 elicits heterogeneous myocardial perfusion that is readily imaged with standard perfusion tracers.

EXAMPLE 2

This example discusses the results from a 12-dog study. The study protocol was similar in that presented in detail in the prior example. The primary differences between the study in Example 1 and that in Example 2 are these. The study in Example 2 is based on a larger population of dogs (n=12) versus compared with the Example 1 study (n=9). Second, and most important, the method of administration of the vasodilator is bolus injection, rather than continuous pump infusion as in Example 1.

The data are displayed in Tables 2 and 3. Table 2 shows data evidencing the efficacy of CGS-21680 versus the gold standard, adenosine. Table 3 displays the relevant hemodynamic parameters, from which one can observe, among other things, the diminished side-effect of reduced blood pressure from CGS-21680 administration compared with adenosine administration.

To the immediate left of the first column are three parameter headings: Cx, LAD, and LAD/Cx. These parameters were defined previously in this Application. Thus, the four rows of data immediately under the uppermost heading, Cx, present flow rates through three regions (Epi, Mid, and Endo) of the circumflex artery (Cx). "Trans" is merely the average flows for the three different regions of the heart wall. Likewise, the four rows under the middle heading, LAD, present flow rates through three regions (plus an average) for the left anterior descending artery. Finally, the lowest heading is LAD/Cx ratio, which simply presents the ratio of the two sets of data presented in the upper portion of the Table.

The first column under each heading is "Baseline 1," which is the resting flow rate. Three columns is "Baseline 2" which is also the resting flow rate, and which is tabulated to demonstrate that the flow has returned to normal (i.e., near the "Baseline 1" value) after adenosine administration, so that CGS-21680 administration can occur without confounding the results through residual adenosine. Thus, the similarity between the Baseline 1 and Baseline 2 numbers reveal that the adenosine has cleared the system, so that the CGS-21680 portion of the study can be performed.

The second and fifth columns report the flow rates after adenosine (column 2) and CGS-21680 (column 2) administration. The third and sixth columns show the "flow reserve" (FR) for adenosine (column 3) and CGS-21680 (column 6). "Flow reserve" is measure in the following way. Flow rate through a given vessel (e.g., Cx) is measured while the heart is at rest, that is, without the administration of a vasodilator. Next, the flow rate is measured after administration of a vasodilator (e.g., either adenosine or CGS-21680). In a normal vessel—i.e., little nor negligible narrowing—the observed increase will be on the order of three to five times the resting flow rate. Indeed, this is evidenced, by comparing of the data in column 2 with the data in column 3. For instance, for the average flow in the circumflex artery, adenosine increased the flow over the average of all regions of the vessel (trans) by over 3 times (1.81/0.56). This ratio is reported in the adjacent column as the flow reserve. For the same vessel, the flow rate increased over 5 times after CGS-21680 administration.

The efficacy of CGS-21680 for enabling the clinician to detect coronary disease are illustrated by two distinct sets of parameters displayed in Table 2: LAD/Cx ratio and flow reserve. In coronary arteries with significant stenosis (>50% luminal diameter narrowing), an inverse relationship exists between the severity of the stenosis and coronary flow reserve. Thus the parameter, flow reserve, is a highly useful parameter in predicting stenosis. The LAD/Cx ratio, discussed previously, reports the ratio of the flow through these two vessels, where an artificial stenosis was induced in the LAD vessel.

The hemodynamic parameters (heart rate and blood pressure) are shown in Table 3. As in the previous Example, these show the reduced side effects-based on change from baseline in these hemodynamic parameters after administration of the agent—from CGS versus adenosine.

each patient. Thus, Example 3 is a hypothetical example, rather than a working example, which presents a protocol based on the method of the present Invention and is based closely upon the dog studies presented above (Examples 2 and 3), and on the adenosine protocol previously developed and approved for use in humans. The adenosine protocol is described in Verani et al., 82 Circulation 80, and provides an exemplary correlation for the skilled cardiologist who desires to design a working protocol based on the method of the present Invention.

First, to a human patient suspected of having coronary disease, CGS-21680 is administered. The method of the

TABLE 2

|  | Baseline 1 | Adenosine | FR during adenosine | Baseline 2 | CGS | FR during CGS |
|---|---|---|---|---|---|---|
| Cx |  |  |  |  |  |  |
| Epi | 0.50 ± 0.14 | 1.85 ± 0.83* | 3.81 ± 1.82 | 0.48 ± 0.18 | 2.31 ± 0.78* | 5.21 ± 1.73a |
| Mid | 0.58 ± 0.16 | 1.91 ± 1.01* | 3.31 ± 1.46 | 0.55 ± 0.19 | 2.09 ± 0.82* | 4.03 ± 1.25 |
| Endo | 0.65 ± 0.22 | 1.63 ± 1.12* | 2.43 ± 1.13 | 0.61 ± 0.20 | 1.56 ± 0.75* | 2.56 ± 0.80 |
| Trans | 0.56 ± 0.17 | 1.81 ± 0.95* | 3.13 ± 1.35 | 0.55 ± 0.18 | 1.99 ± 0.77* | 3.79 ± 1.08 |
| LAD |  |  |  |  |  |  |
| Epi | 0.47 ± 0.16 | 0.74 ± 0.40** | 1.65 ± 0.94 | 0.51 ± 0.20 | 0.81 ± 0.45# | 1.77 ± 1.08 |
| Mid | 0.46 ± 0.13 | 0.50 ± 0.31 | 1.08 ± 0.57 | 0.49 ± 0.21 | 0.47 ± 0.24 | 1.05 ± 0.56 |
| Endo | 0.48 ± 0.19^ | 0.44 ± 0.37 | 0.86 ± 0.48 | 0.50 ± 0.19 | 0.37 ± 0.29 | 0.79 ± 0.55 |
| Trans | 0.47 ± 0.15 | 0.56 ± 0.33 | 1.19 ± 0.58 | 0.50 ± 0.18 | 0.54 ± 0.27 | 1.17 ± 0.62 |
| LAD/Cx ratio |  |  |  |  |  |  |
| Epi | 96% ± 22% | 40% ± 12%* |  | 113% ± 39% | 35% ± 14%* |  |
| Mid | 80% ± 12% | 27% ± 10%* |  | 95% ± 38% | 23% ± 9%* |  |
| Endo | 74% ± 16% | 28% ± 13%* |  | 84% ± 28% | 24% ± 12%* |  |
| Trans | 82% ± 14% | 32% ± 11%* |  | 96% ± 32% | 27% ± 10%* |  |

*$p < 0.005$ vs. baseline;
**$p < 0.05$ vs. baseline;
$p = 0.05$ vs. baseline
a, $p < 0.05$ vs. baseline
^, $p < 0.05$ vs. Cx

TABLE 3

|  | Baseline 1 | Adenosine | Δ | Baseline 2 | CCGS | Δ |
|---|---|---|---|---|---|---|
| HR | 125 ± 26 | 112 ± 25 | −12 ± 21 | 113 ± 21 | 137 ± 33* | 24 ± 22** |
| Systolic AP | 125 ± 19 | 89 ± 23* | −36 ± 9 | 120 ± 18 | 106 ± 23* | −14 ± 10** |
| Diastolic AP | 99 ± 15 | 62 ± 16* | −37 ± 10 | 96 ± 16 | 70 ± 14* | −26 ± 10# |

*, $p < 0.005$ vs. baseline
**, $p < 0.005$;
, $p < 0.05$ vs. change during adenosine

EXAMPLE 3

Based on the examples just presented, the design of a protocol based on the method of the present Invention for use in detecting coronary disease in humans is well within the knowledge and skill possessed by the ordinary skilled cardiologist. Based on the information provided in the present Specification, particularly that provided in Examples 1–3, coupled with the knowledge and skill possessed by the skilled cardiologist, the skilled cardiologist could readily design a working protocol to assess myocardial perfusion or dysfunction in patients, utilizing the method of the present Invention, without undue experimentation. Moreover, the skilled cardiologist readily recognizes the futility of reciting a single set of parameters (e.g., total dose, duration of dose, etc.) since these parameters will require slight adjustment for present Invention teaches two ways of administering CGS-21680. The first method is the current one for administering adenosine: continuous pump infusion. The relatively brief half-life ($t_{1/2}$) of adenosine compels the need for this means of administration. By contrast, CGS-21680 has a significantly longer $t_{1/2}$, therefore it can be injected as a bolus.

For continuous infusion, the skilled clinician begins administration of a dose of about 0.25 μg/kg/min and increases it every three minutes to a probably maximum of about 2.5 μg/kg/min, while closely monitoring the patient's hemodynamic parameters and symptoms evidencing tolerance of lack of tolerance.

The second method of injection is a bolus injection. Such a single injection is preferably done slowly over a period of approximately five minutes. The optimal dose will vary, though a dosage range of between about 0.25 μg/kg/min and 2.5 μg/kg/min given about three minutes is suggested. The skilled clinician can readily identify the optimal dose by beginning with a low dose then carefully increasing the does while monitoring the patient.

What is claimed is:

1. A method for determining myocardial perfusion and dysfunction comprising administering to a patient suspected of having coronary artery disease, the compound CGS-21680, in an amount appropriate to achieve near maximum coronary vasodilation.

2. The method of claim 1 comprising the additional step of identifying the presence of coronary disease by perfusion scintigraphy or contrast echocardiography (or other imaging modalities).

3. The method of claim 2 wherein said scintigraphy is performed using single-photon tracers selected from the group consisting of thallium-201, $^{99m}$Tc sestamibi, $^{99m}$Tc teboroxime, and $^{99m}$Tc tetrofosmin.

4. The method of claim 2 wherein said scintigraphy is performed using positron emitters selected from the group consisting of oxygen-15 water, nitrogen-13 ammonia, or rubidium-82.

5. A method for assessing myocardial function (cardiac contraction or wall motion) in a mammal comprising:

administering to said mammal a compound, or a salt thereof, having the formula wherein R' represents hydrogen or $C_1$–$C_4$-alkyl; $R_1$' represents ($C_5$– or C6)-cycloalkyl-$C_1$–$C_4$-alkyl, or $R_1$' represents aryl-$C_1$–$C_4$ alkyl in which aryl represents 2- or 3-thienyl, 2-, 3- or 4-pyridyl, phenyl, or phenyl monosubstituted by halogen, trifluoromethyl, lower alkoxy, lower alkyl or by a substituent—W-Z in which W represents a direct bond, $C_1$–$C_4$-alkylene, thio-$C_1$–$C_3$-alkylene or oxy-$C_1$–$C_3$-alkylene and Z represents cyano, carboxy, lower alkoxycarbonyl, carbamoyl, N-mono- or N,N-di-lower alkylcarbamoyl; or $R_1$' represents aryl-hydroxy-$C_1$–$C_4$-alkyl in which aryl has meaning as defined above; $R_4$' represents $C_1$–$C_4$-alkyl, cyclopropyl or hydroxy-$C_2$–$C_4$-alkyl; $R_5$ and $R_6$ represent hydrogen, lower alkanoyl, lower alkoxy-lower alkanoyl, aroyl, carbamoyl, or mono- or di-lower alkylcarbamoyl; or a pharmaceutically acceptable salt thereof, measuring myocardial function in said mammal.

6. The method of claim 5 wherein said compound is 2-p-(2-Carboxymethyl)phenethylamino-5'-N-ethylcarboxamidoadenosine hydrochloride.

7. The method of claim 5 wherein said measuring step is myocardial scintigraphy.

8. The method of claim 5 comprising the additional step of injecting said mammal with a myocardial perfusion imaging agent.

9. The method of claim 8 wherein said myocardial perfusion imaging agent is selected from the group consisting of thallium-201, $^{99m}$Tc sestamibi, $^{99m}$Tc teboroxime, and $^{99m}$Tc tetrofosmin.

10. The method of claim 8 wherein said agent is administered by injection between about 1 and 15 minutes after the maximum concentration, in the case of continuous infusion.

11. The method of claim 8 wherein said agent is administered by injection between about 1 to 15 minutes after the administration of the compound, in the case of bolus injection.

12. The method of claim 8 wherein said compound is administered for between about 1 and 4 minutes after administration of the agent.

13. The method of claim 5 wherein said measuring step comprises assessing myocardial blood flow by determining the ratio of the left anterior descending artery flow over the circumflex artery flow.

14. The method of claim 5 wherein said measuring step is myocardial perfusion imaging.

15. The method of claim 12 wherein said myocardial imaging is a technique selected from the group consisting of planar scintigraphy, single photon emission computed tomography, positron emission tomography, nuclear magnetic resonance imaging, myocardial contrast echocardiography, digital subtraction angiography, and ultrafast (electron-beam) x-ray computed tomography.

16. The method of claim 13 wherein said myocardial perfusion imaging is performed immediately after administration of said compound.

17. The method of claim 14 comprising the additional step of obtaining a second imaging wherein said imaging is performed between about 1 and about 6 hours after administration of said compound.

18. The method of claim 5 wherein said myocardial function is measured during substantially maximum coronary vasodilation.

19. The method of claim 5 wherein said mammal is administered said compound by continuous infusion over a period of between about 2 and 10 minutes.

20. The method of claim 10 wherein said compound is administered at a rate of between about 25 and 150 μg/kg/min.

21. The method of claim 5 wherein said mammal is administered said compound by bolus injection.

22. The method of claim 19 wherein said compound is administered between about 100 and 500 μg.

23. A method for assessing myocardial function in a mammal comprising:

administering to said mammal the compound 2-p-(2-carboxymethyl)phenethylamino-5'-N-ethylcarboxamidoadenosine hydrochloride in sufficient quantity to produce vasodilation; thereafter measuring myocardial function in said mammal.

* * * * *

UNITED STATES PATENT AND TRADEMARK OFFICE
CERTIFICATE OF CORRECTION

PATENT NO. : 6,026,317

DATED : Feb. 15, 2000

INVENTOR(S) : Mario S. Verani

It is certified that error appears in the above-identified patent and that said Letters Patent is hereby corrected as shown below:

Column 1, line 13, delete "whom" and insert -- who --
Column 3, lines 1-2, delete "[$^3$H]CGS 21680, a selective $A_2$ receptor agonist directly labels $A_2$ receptors in rat brain" and insert in italics -- *[$^3$H]CGS 21680, a selective $A_2$ receptor agonist directly labels $A_2$ receptors in rat brain*
Column 3, line 58, delete "Ciga" and insert -- Ciba --
Column 4, line 16 after "insufficient" insert -- to --
Column 4, line 64, delete "resources" and insert -- resonance --
Column 5, line 21, delete "clinical" and insert -- clinician --
Column 5, line 27, delete "the" and insert -- by --
Column 5, line 59, delete "be"
Column 6, line 26, delete "chose" and insert -- chosen --
Column 6, line 38, delete "return" and insert -- returned --
Column 6, line 43, delete "is" and insert -- was --
Column 7, line 2, delete "will"
Column 7, line 43, delete "GS-21680" and insert -- CGS-21680 --
Column 7, line 56, delete "LAD/Cs" and insert -- LAD/Cx --
Column 7, line 56, delete "perfusion's agent" and insert -- perfusion agent's --
Column 7, line 62, after "rate" insert -- , --
Column 8, line 7, delete the first occurrence of "in"

UNITED STATES PATENT AND TRADEMARK OFFICE
CERTIFICATE OF CORRECTION

PATENT NO. : 6,026,317

DATED : Feb. 15, 2000

INVENTOR(S) : Mario S. Verani

It is certified that error appears in the above-identified patent and that said Letters Patent is hereby corrected as shown below:

Column 8, line 11, delete "versus"
Column 8, line 36, after "columns" insert - - over - -
Column 8, line 46, delete the second occurrence of "(column 2)" and insert - - (column 5) - -
Column 8, line 49, delete "measure" and insert - - measured - -
Column 8, line 54, delete "nor" and insert - - or - -
Column 10, line 63, delete the first occurrence of "of" and insert - - or - -

Column 11, line 3, delete "does" and insert - - dose - -
Column 11, line 26, after "formula" insert the following formula - -

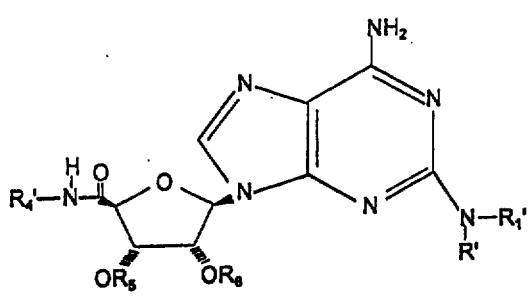

Signed and Sealed this

Twenty-seventh Day of March, 2001

Attest:

NICHOLAS P. GODICI

Attesting Officer

Acting Director of the United States Patent and Trademark Office